(12) United States Patent
Nicks

(10) Patent No.: US 10,669,044 B2
(45) Date of Patent: Jun. 2, 2020

(54) SERVICE TROLLEY FOR INSPECTING AN INTERIOR CABIN OF A VEHICLE

(71) Applicant: The Boeing Company, Chicago, IL (US)

(72) Inventor: Eric Nicks, Defiance, MO (US)

(73) Assignee: The Boeing Company, Chicago, IL (US)

( * ) Notice: Subject to any disclaimer, the term of this patent is extended or adjusted under 35 U.S.C. 154(b) by 118 days.

(21) Appl. No.: 16/053,078

(22) Filed: Aug. 2, 2018

(65) Prior Publication Data
US 2020/0039664 A1 Feb. 6, 2020

(51) Int. Cl.
| | |
|---|---|
| *B64F 5/60* | (2017.01) |
| *B64D 11/00* | (2006.01) |
| *G07C 5/00* | (2006.01) |
| *G07C 5/08* | (2006.01) |
| *G01K 13/00* | (2006.01) |
| *G01N 33/00* | (2006.01) |
| *G05D 1/00* | (2006.01) |
| *B64D 13/08* | (2006.01) |
| *B64D 11/06* | (2006.01) |
| *B64D 13/06* | (2006.01) |
| *G06T 7/00* | (2017.01) |

(52) U.S. Cl.
CPC .......... *B64F 5/60* (2017.01); *B64D 11/0007* (2013.01); *G01K 13/00* (2013.01); *G01N 33/0036* (2013.01); *G05D 1/0088* (2013.01); *G07C 5/008* (2013.01); *G07C 5/085* (2013.01); *G07C 5/0808* (2013.01); *B64D 11/00* (2013.01); *B64D 11/0015* (2013.01); *B64D 11/064* (2014.12); *B64D 13/06* (2013.01); *B64D 13/08* (2013.01); *B64D 2011/0053* (2013.01); *B64D 2013/0603* (2013.01); *G05D 2201/0207* (2013.01); *G06T 7/001* (2013.01); *G06T 2207/30268* (2013.01)

(58) Field of Classification Search
CPC ........ B64F 5/60; G01K 13/00; G05D 1/0088; G05D 2201/0207; G07C 5/0808; G07C 5/008; G07C 5/085; G01N 33/0036; B64D 2011/0053; B64D 11/064; B64D 11/00; B64D 13/06; B64D 2013/0603; B64D 11/0015; B64D 11/0007; B64D 13/08; G06T 7/001; G06T 2207/30268
See application file for complete search history.

(56) References Cited

U.S. PATENT DOCUMENTS

| | | | |
|---|---|---|---|
| 7,444,830 B2 * | 11/2008 | Moran .................. | F25D 11/003 374/E11.006 |
| 8,596,654 B2 * | 12/2013 | Belanger ................ | B62B 3/004 280/47.34 |

* cited by examiner

*Primary Examiner* — Rodney A Butler
(74) *Attorney, Agent, or Firm* — Vivacqua Law, PLLC

(57) ABSTRACT

A service trolley for inspecting an interior cabin of a vehicle including a plurality of seats is disclosed. The service trolley includes a container body supported by a plurality of wheels, at least one image capture device, and a control module in communication with the image capture device and a database. The image capture device is mounted to the container body and is positioned along an outer surface of the container body in a location relative to the interior cabin of the vehicle to view the plurality of seats. The database stores image data of the plurality of seats of the vehicle. The control module executes instructions to compare the image data stored in the database with the image of a specific seat to determine a presence of at least one defect on an exterior of a specific seat in the interior cabin of the vehicle.

20 Claims, 6 Drawing Sheets

SERVICE TROLLEY FOR INSPECTING AN INTERIOR CABIN OF A VEHICLE

The present disclosure relates to a service trolley, and more particularly to a service trolley for inspecting an interior cabin of a vehicle.

BACKGROUND

Some airlines dispatch several personnel to inspect the interior cabin of an aircraft on a periodic basis. For example, six trained employees may be dispatched to inspect the interior cabin of an aircraft, which usually takes about two hours. The interior cabin may be inspected daily or every two days, while other airlines may inspect the interior cabin on a more infrequent basis or not at all. The personnel may inspect various systems that passengers utilize while the aircraft is in flight such as, for example, seating, overhead reading lights, environmental cabin control, personal entertainment devices, and other components within the interior cabin to ensure they are in working order. For example, the personnel may visually inspect the seats for rips or tears in the upholstery. In another example, the personnel may confirm that the back of the seat actuates between a reclined and an upright position. The personnel may also confirm that the interior and energy lights are in working order and illuminate when a switch is selected.

It is to be appreciated that the personnel perform these tasks manually. For example, someone needs to press a button or selector to actuate the seat into the reclined and back into the upright position. In another example, someone also needs to flip each lighting switch on and off to confirm the overhead reading lights are functioning. Accordingly, inspecting the aircraft cabin may be tedious, time consuming, and incurs significant labor costs. However, foregoing the inspection may result in cabin maintenance issues that some passenger may notice and results in lower customer satisfaction.

SUMMARY

According to several aspects, a service trolley for inspecting an interior cabin of a vehicle including a plurality of seats is disclosed. The service trolley includes a container body supported by a plurality of wheels, where the service trolley defines an outer surface. The service trolley also includes at least one image capture device mounted to the container body and positioned along the outer surface of the container body in a location relative to the interior cabin of the vehicle to view the plurality of seats. The service trolley also includes a control module in electronic communication with the image capture device. The control module is in electronic communication with a database storing image data representative of the plurality of seats of the vehicle. The control module executes instructions to receive an image of a specific seat from the at least one image capture device and compare the image data stored in the database with the image of the specific seat to determine a presence of at least one defect on an exterior of the specific seat in the interior cabin of the vehicle. In response to determining the presence of at least one defect along an exterior of one of the plurality of seats, the control module generates an error code indicating the presence of the at least one defect on the exterior of the specific seat.

According to several aspects, a method of inspecting an interior cabin of a vehicle including a plurality of seats by a service trolley is disclosed. The method includes receiving, by a control module of the service trolley, an image of a specific seat from at least one image capture device. The image capture device is mounted to a container body of the service trolley is and positioned along an outer surface of the container body in a location relative to the interior cabin of the vehicle to view the plurality of seats. The method also includes comparing, by the control module of the service trolley, image data stored in a database with the image of the specific seat to determine a presence of at least one defect on an exterior of the specific seat in the interior cabin of the vehicle. In response to determining the presence of at least one defect along an exterior of one of the plurality of seats, the method includes generating an error code indicating the presence of the at least one defect on the exterior of the specific seat.

The features, functions, and advantages that have been discussed may be achieved independently in various embodiments or may be combined in other embodiments further details of which can be seen with reference to the following description and drawings.

BRIEF DESCRIPTION OF THE DRAWINGS

The drawings described herein are for illustration purposes only and are not intended to limit the scope of the present disclosure in any way.

DETAILED DESCRIPTION

The present disclosure is directed towards a service trolley configured to inspect an interior cabin of a vehicle. The vehicle is any moveable conveyance for transporting passengers that includes a plurality of seats arranged within the interior cabin such as, but not limited to, an aircraft. The service trolley includes image capture devices for viewing seats located within the interior cabin of the vehicle. The service trolley travels within the aisleway of the interior cabin to inspect the exterior of the seats for at least one or defect or irregularity such as, for example, rips or tears in the upholstery. The service trolley also inspects each seat to ensure an actuator for reclining the seat is functional. The service trolley also inspects the electronic systems associated with each seat within the interior cabin of the vehicle. In one embodiment, the service trolley is autonomously or semi-autonomously controlled to navigate the interior cabin of the vehicle. The disclosed service trolley provides an automated approach for inspecting the interior cabin of the vehicle.

The following description is merely exemplary in nature and is not intended to limit the present disclosure, application, or uses.

Figure 1:
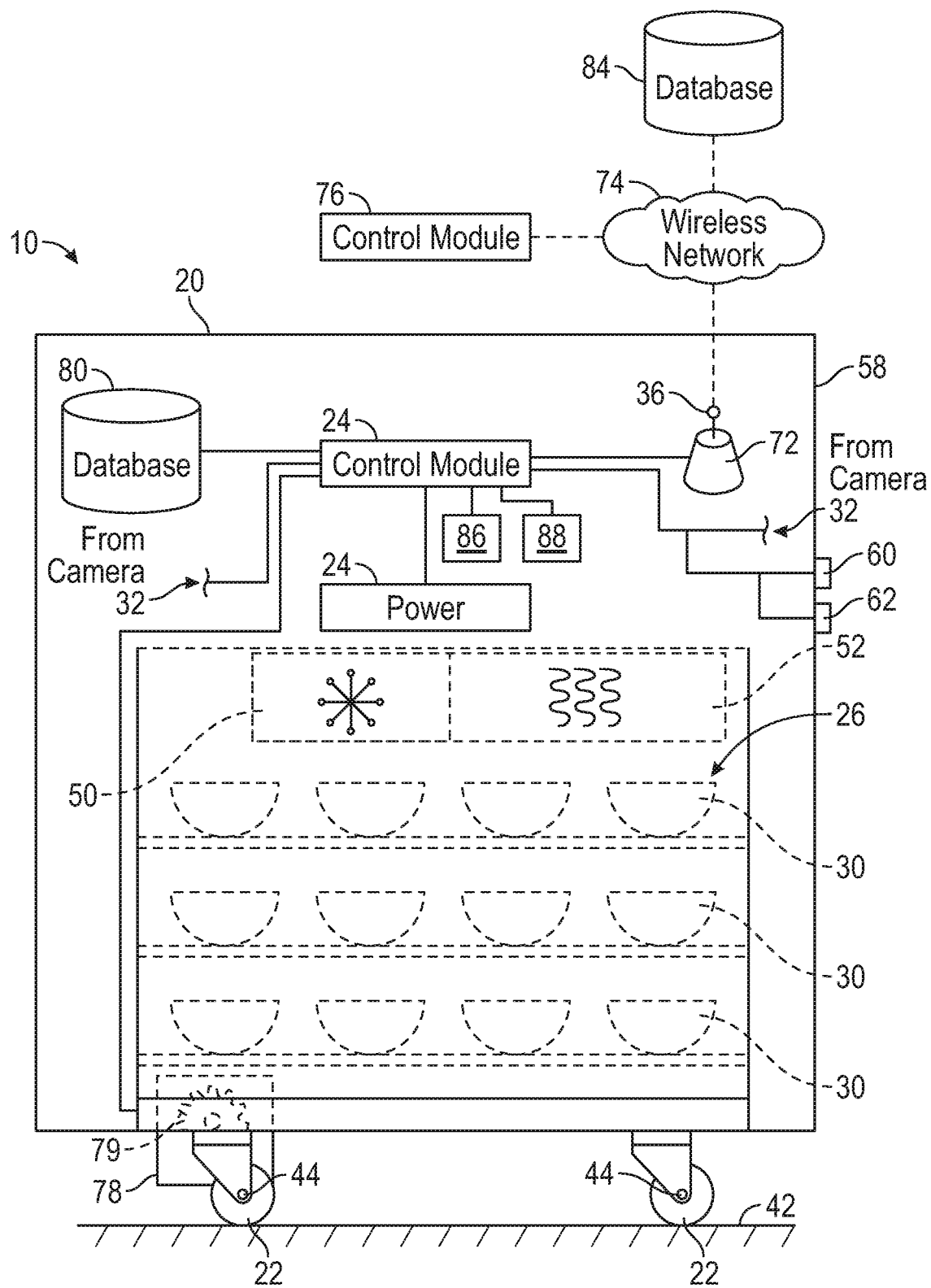
FIG. 1 is a schematic diagram of an exemplary service trolley for inspecting a vehicle interior according to an exemplary embodiment.

Referring to FIG. 1, an exemplary service trolley 10 for inspecting an interior cabin of a vehicle is disclosed. In an embodiment, the service trolley 10 transports items such as, for example, beverages, meals, blankets, pillows, and headphones that are used by passengers of the vehicle. The service trolley 10 includes a container body 20 supported by a plurality of wheels 22, a power source 24, at least one compartment 26 for storing items 30, at least one image capture device 32 (FIG. 2) mounted to the container body 20, an antenna 36, and a control module 40. The container body 20 is supported by the wheels 22 relative to a support surface or the ground 42. The wheels 22 of the service trolley 10 are configured to rotate about their respective axes 44, thereby propelling the service trolley 10 along the ground 42.

In one non-limiting embodiment, the items 30 are food, beverages, or both. Accordingly, a cooling unit 50 is provided to keep cold beverages and food refrigerated. Similarly, a heating unit 52 may also be provided to keep hot beverages and food heated. However, it is to be appreciated that the cooling unit 50 and the heating unit 52 are optional components. For example, if the service trolley 10 is used to transport non-perishable items such as, for example, headphones or blankets, then the cooling unit 50 and the heating unit 52 are not needed.

Figure 2:
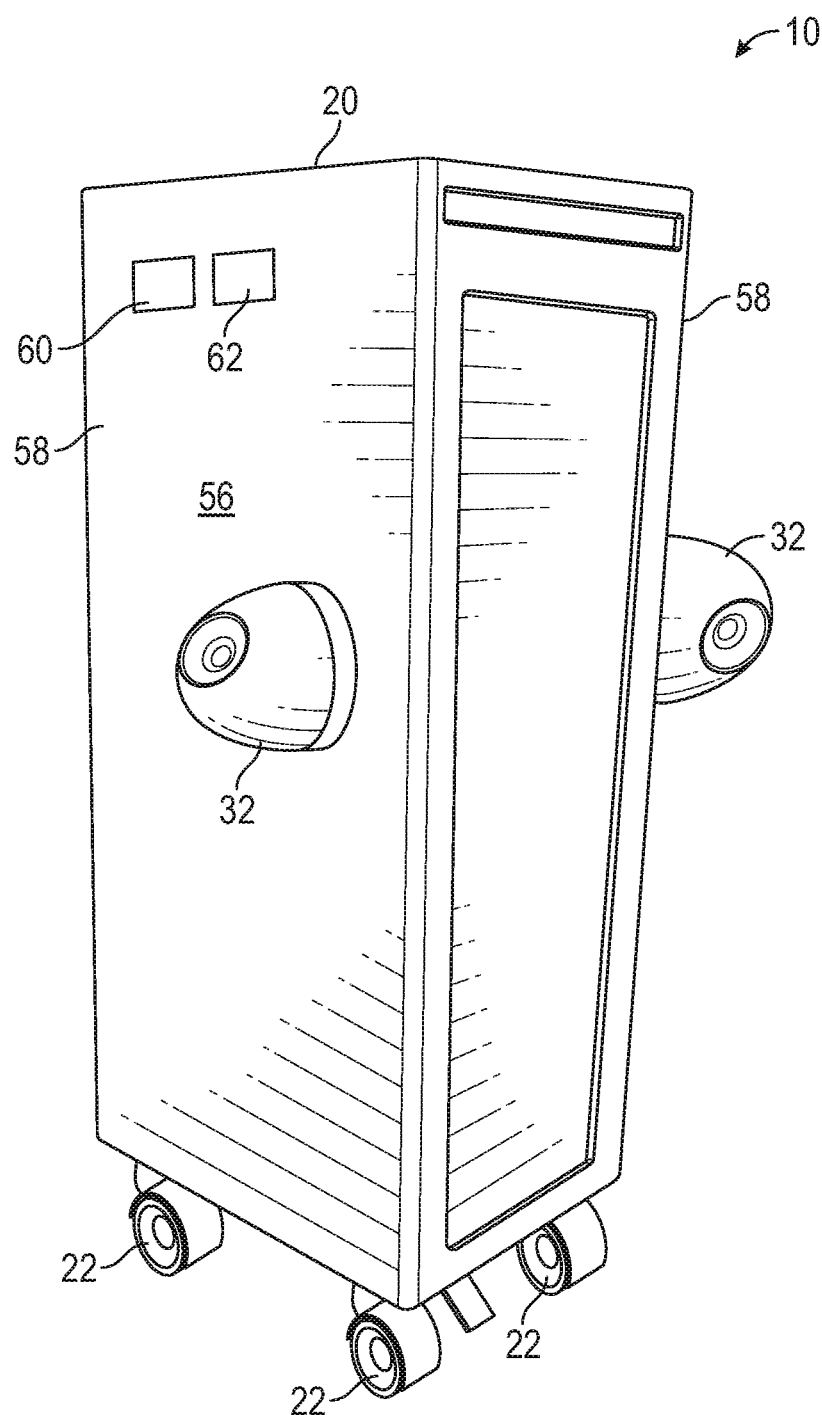
FIG. 2 is a perspective view of the service trolley shown in FIG. 1 including two image capture devices according to an exemplary embodiment.

FIG. 2 is a perspective view of the service trolley 10 shown in FIG. 1. In the embodiment as illustrated, the container body 20 defines an outer surface 56. The outer surface 56 of the container body 20 includes opposing side surfaces 58, where a thermocouple or temperature sensor 60 and a humidity sensor 62 are mounted to the outer surface 56 of the service trolley 10. Although the temperature sensor 60 and the humidity sensor 62 are shown mounted to the same side surface 58, it is to be appreciated that FIG. 2 is merely exemplary in nature.

In the embodiment as shown in FIG. 2, a single image capture device 32 is mounted to each side surface 58 of the service trolley 10. The image capture devices 32 include any device configured to capture imagery such as still photographs or moving video. In one embodiment, the image capture devices 32 are both 180-degree cameras (i.e., there is a right-hand camera and a left-hand camera). Accordingly, when the images from both cameras are combined by image processing techniques, an entire 360-degree view of the interior cabin is provided.

Referring to FIG. 1, the antenna 36 is in electronic communication with a transceiver 72. The antenna 36 is sized to receive and send short-range wireless signals and is configured to connect with a wireless network 74 of the vehicle. The wireless network 74 is configured to communicate data between the control module 40 of the service trolley 10 and one or more control modules 76 on the vehicle. The short-range wireless signal is any type of wireless signal configured to exchange data over relatively short distances (e.g., about ten meters). Some examples of short-range wireless protocol signals include, for example, a signal conforming to the Institute of Electrical and Electronics Engineers (IEEE) Standard 802.15 or a signal conforming to IEEE standard 802.11. Although FIG. 1 illustrates the transceiver 72 and the antenna 36 as separate components from the control module 40, in another embodiment the transceiver 72 and the antenna 36 are integrated with the control module 40 instead.

The service trolley 10 also includes a wheel assist device 78 in communication with the control module 40 and is configured to control rotation of the wheels 22. The wheel assist device 78 includes a motor 79 for generating the motion required to urge the wheels 22 to rotate in a specific direction. Urging the wheels 22 in a specific direction propels the service trolley 10 in the same direction. The wheel assist device 78 also provides braking for inhibiting the wheels 22 from rotating in a given direction. In one embodiment, the wheel assist device 78 is configured to autonomously control the service trolley 10 by manipulating the wheels 22, without any human intervention. In another embodiment, the wheel assist device 78 is configured to manipulate the wheels 22 of the service trolley 10 with some human interaction or input, but also performs some maneuvers as well. In other words, the service trolley 10 is maneuvered semi-autonomously.

Although FIG. 1 illustrates the wheel assist device 78, in an alternative embodiment the wheel assist device 78 is omitted. Instead, the service trolley 10 is manipulated by a person. For example, if the vehicle is an aircraft a flight attendant maneuvers the service trolley 10 about the interior cabin. However, when the aircraft is grounded, then the service trolley 10 is maneuvered by a crew member inspecting the interior cabin of the aircraft. Inspection of the interior cabin of the aircraft is explained in greater detail below. Although it is possible to manipulate the service trolley 10 by a person, operating the service trolley 10 autonomously or semi-autonomously reduces the work required by crew members or other personnel who are responsible for inspecting the interior cabin of the vehicle.

In one embodiment, the power source 24 of the service trolley 10 provides energy to the wheel assist device 78. The power source 24 also provides power to the image capture device 32, the control module 40, the cooling unit 50, the heating unit 52, and any other devices that require electrical power. The power source 24 is any device for supplying electrical power to various components within the service trolley 10 such as, for example, a battery. Alternatively, in another embodiment the power source 24 is omitted and instead electrical power is harvested from another source.

Referring to both FIGS. 1 and 2, the control module 40 of the service trolley 10 is in electronic communication with the power source 24, the image capture devices 32 (FIG. 2), the transceiver 72 of the antenna 36, the temperature sensor 60, the humidity sensor 62, and a memory or database 80. The control module 40 is a non-generalized, electronic control device having a preprogrammed digital computer or processor, memory or non-transitory computer readable medium used to store data such as control logic, instructions, image data, lookup tables, etc., and a plurality of input/output peripherals or ports. The processor of the control module 40 is configured to execute the control logic or instructions. In one embodiment, the control module 40 is an electronic control unit (ECU).

Although FIG. 1 illustrates a single control module 40, more than one control module may be used as well. Furthermore, although FIG. 1 illustrates the control module 40 and the database 80 as separate objects, in another embodiment the database 80 is integrated with the control module 40. Alternatively, the database 80 is stored remotely on a database 84 of the vehicle and is accessed by the control module 40 by the wireless network 74.

Figure 3:
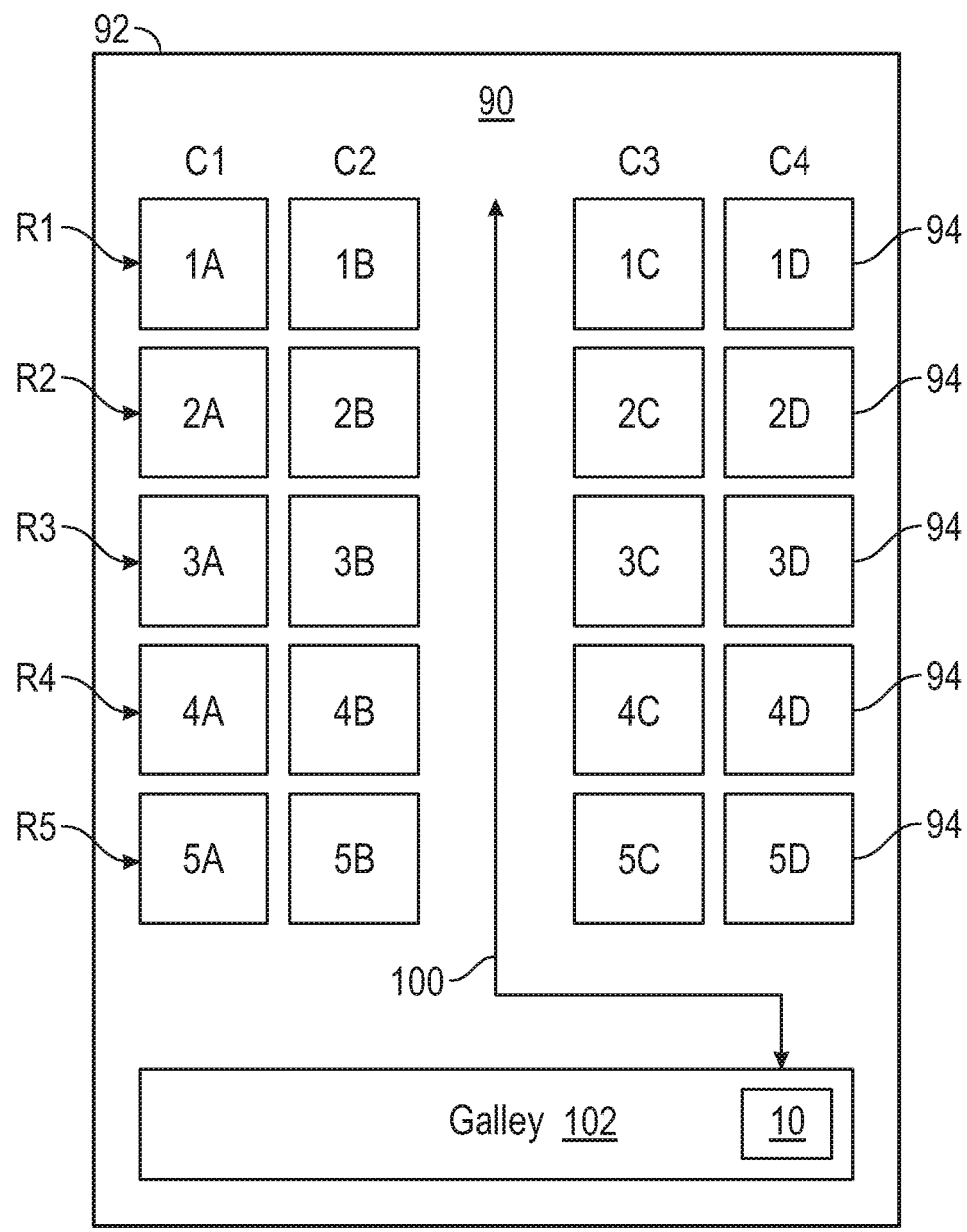
FIG. 3 is a schematic diagram of an interior cabin of an aircraft including the service trolley placed in the galley according to an exemplary embodiment.

FIG. 3 is an exemplary diagram of an interior cabin 90 of a vehicle 92. A plurality of seats 94 are located within the interior cabin 90 are arranged in rows R and columns C to define an aisleway 100. The aisleway 100 is sized to accommodate the service trolley 10. In other words, the service trolley 10 fits within the aisleway 100 without interfering with the seats 94. In the exemplary embodiment as shown, the seats 94 are arranged into five rows R1-R5 and four columns C1-C4, where the aisleway 100 is located between columns C2 and C3. The vehicle 92 is any type of conveyance for transporting passengers that includes a plurality of seats. In the example as shown in FIG. 3, the vehicle 92 is an aircraft. However, in other embodiments the vehicle 92 is a train, a bus, or another land vehicle. If the vehicle 92 is an aircraft, then the service trolley 10 is sometimes referred to as an airline service trolley. Furthermore, because the service trolley 10 is normally stowed in a galley 102 of the aircraft, the service trolley 10 is sometimes referred to as a galley cart.

In the non-limiting embodiment as shown, the interior cabin 90 of the vehicle 92 includes twenty seats 94. However, it is understood that only twenty seats 94 are illustrated for the purposes of simplicity and clarity and that the vehicle 92 may include any number of seats. For example, if the vehicle 92 is a large passenger aircraft the interior cabin 90 includes about 386 seats. As seen in FIG. 3, each seat 94 is assigned a unique seat number. The seat number indicates the relative position of a specific seat 94 within the interior cabin 90 of the vehicle 92. For example, in the embodiment as illustrated each seat number includes a first character that is a number and a second character that is a letter. The first character is a number designating the row number (i.e., rows 1-5) and the second character is a letter designing the column (i.e., columns A-D). Therefore, the seat 94 located in the first row R1 and in the second column C2 is designated as seat number 1B.

Referring to FIGS. 1 and 3, the image capture devices 32 are mounted to the container body 20 and are positioned along the outer surface 56 of the container body 20 in a location relative to the interior cabin 90 of the vehicle 92 to view the plurality of seats 94. The service trolley 10 also includes a position sensor 86 and an accelerometer 88 in electronic communication with the control module 40. The position sensor 86 provides a positional signal to the control module 40 of the service trolley 10 for indicating relative position with the interior cabin 90 of the vehicle 92. For example, in an embodiment the positional signal indicates the service trolley 10 is stowed in the galley 102. The accelerometer 88 generates a motion signal in response to detecting movement of the service trolley 10. For example, as the service trolley 10 is removed from the galley 102, the motion signal is generated.

Referring to both FIGS. 1 and 3, the database 80 stores image data that represents the plurality of seats 94 of the vehicle 92. In one non-limiting embodiment, each of the seats 94 of the vehicle 92 include a substantially uniform outer appearance. That is, every seat 94 located within the vehicle 92 includes the same color and type of upholstery (i.e., cloth, leather, etc.), the same headrest, and the same seat cushions. Alternatively, in another embodiment each section of the vehicle 92 includes seats 94 with different appearances. For example, seating in a first class compartment typically includes larger seats compared to seating in economy. Accordingly, the database 80 stores image data representative of the different types of seating in the vehicle 92 as well. Furthermore, in an embodiment the database 80 stores image data pertaining to the seating of multiple types of vehicles. For example, if the vehicle 92 is a large passenger aircraft, then the database 80 stores image data representative of seating in first class and economy of the large passenger aircraft as well as image data pertaining to the seating in other aircraft models as well. In one embodiment, in addition to the images of the seats the database 80 also stores images representative of other interior components such as, for example, overhead bins and other furnishings within the interior cabin 90.

In the embodiment as shown, the service trolley 10 is normally stowed in the galley 102 of the vehicle 92. The service trolley 10 is moved out of the galley 102 and travels through the aisleway 100 to inspect the plurality of seats 94 located within the interior cabin 90 of the vehicle 92. For example, if the vehicle 92 is an aircraft, the service trolley 10 is removed from the galley 102 during flight and moves along the aisleway 100 to serve beverages, meals, and other items to passengers. In some embodiments, a flight attendant may push the service trolley 10 through the aisleway 100 when serving passengers. The service trolley 10 is also removed from the galley 102 when the aircraft is grounded. Specifically, the service trolley 10 travels through the aisleway 100 to inspect the seats 94 when the aircraft is grounded. For example, in one embodiment the service trolley 10 first inspects the seats 94 located in the fifth row R5. The service trolley 10 then travels along the aisleway 100 to the next row of seats, which is the fourth row R4. This process may continue until the service trolley 10 reaches the first row R1 and inspects all the seats 94 within the interior cabin 90.

The service trolley 10 inspects the seats 94 when the vehicle 92 is stationary as well as when the vehicle 92 is traveling. When stationary, the vehicle 92 does not move substantially. For example, an aircraft is stationary when grounded. When the vehicle 92 is traveling, the vehicle 92 is moving from an origin to a destination. For example, an aircraft is in flight when traveling. As explained below, when the vehicle 92 is station or traveling, the service trolley 10 inspects the interior cabin 90 of the vehicle 92 to determine the presence of one or more defects on an exterior of a specific seat 94 in the interior cabin 90 of the vehicle 92. Once the specific seat 94 is inspected, the service trolley 10 then inspects another seat 94 adjacent to or proximate to the seat 94 that was just inspected. For example, the service trolley 10 first inspects seat 5A, and then continues by inspecting seats 5B, 5C, and 5D. Once the trolley finishes inspecting seat 5D, the service trolley 10 then moves forward and inspects seat 4A. This process continues until all the seats 94 within the interior cabin 90 are inspected.

Figure 4:
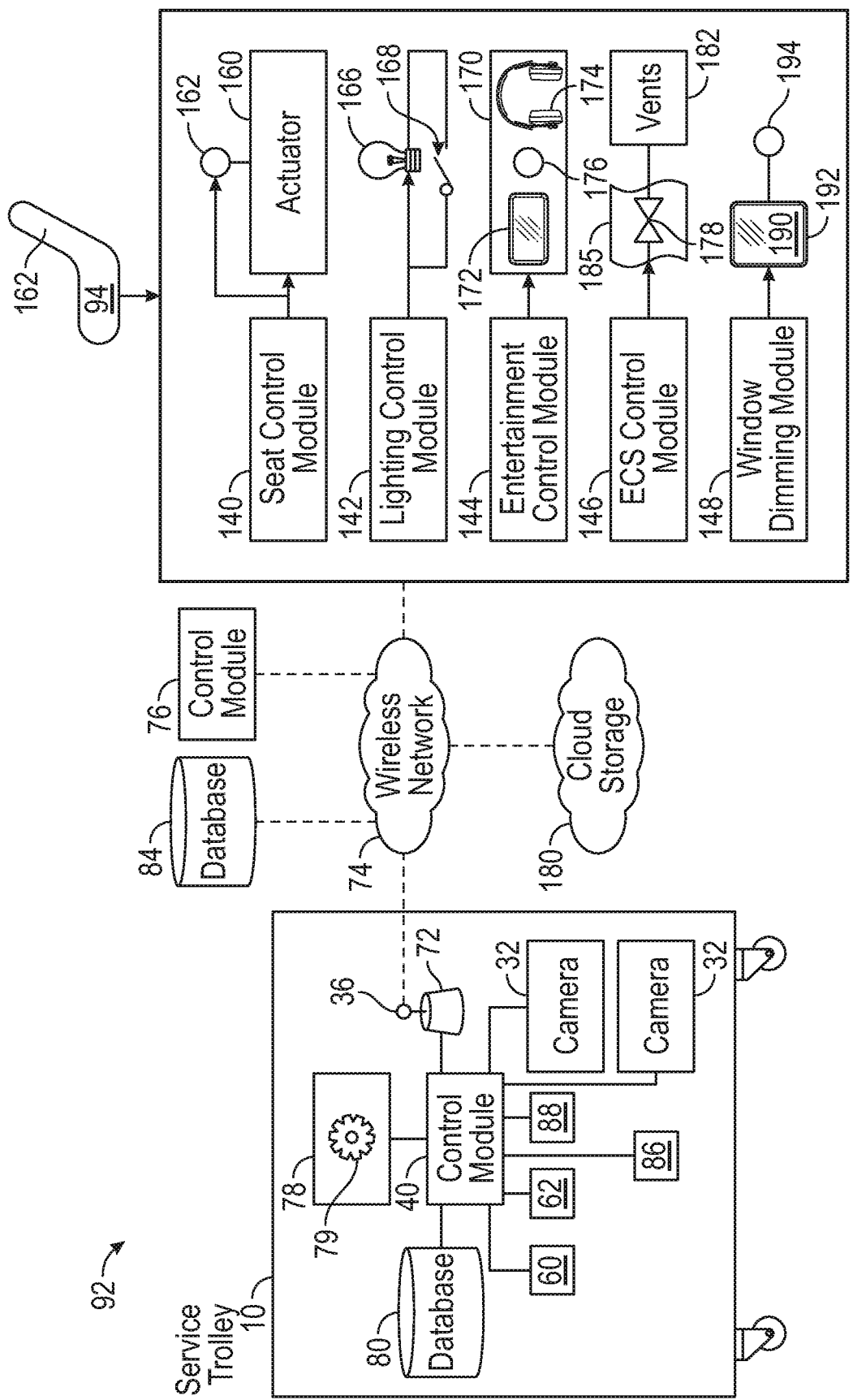
FIG. 4 is a schematic diagram of a control system for operating the service trolley according to an exemplary embodiment.
Figure 5:
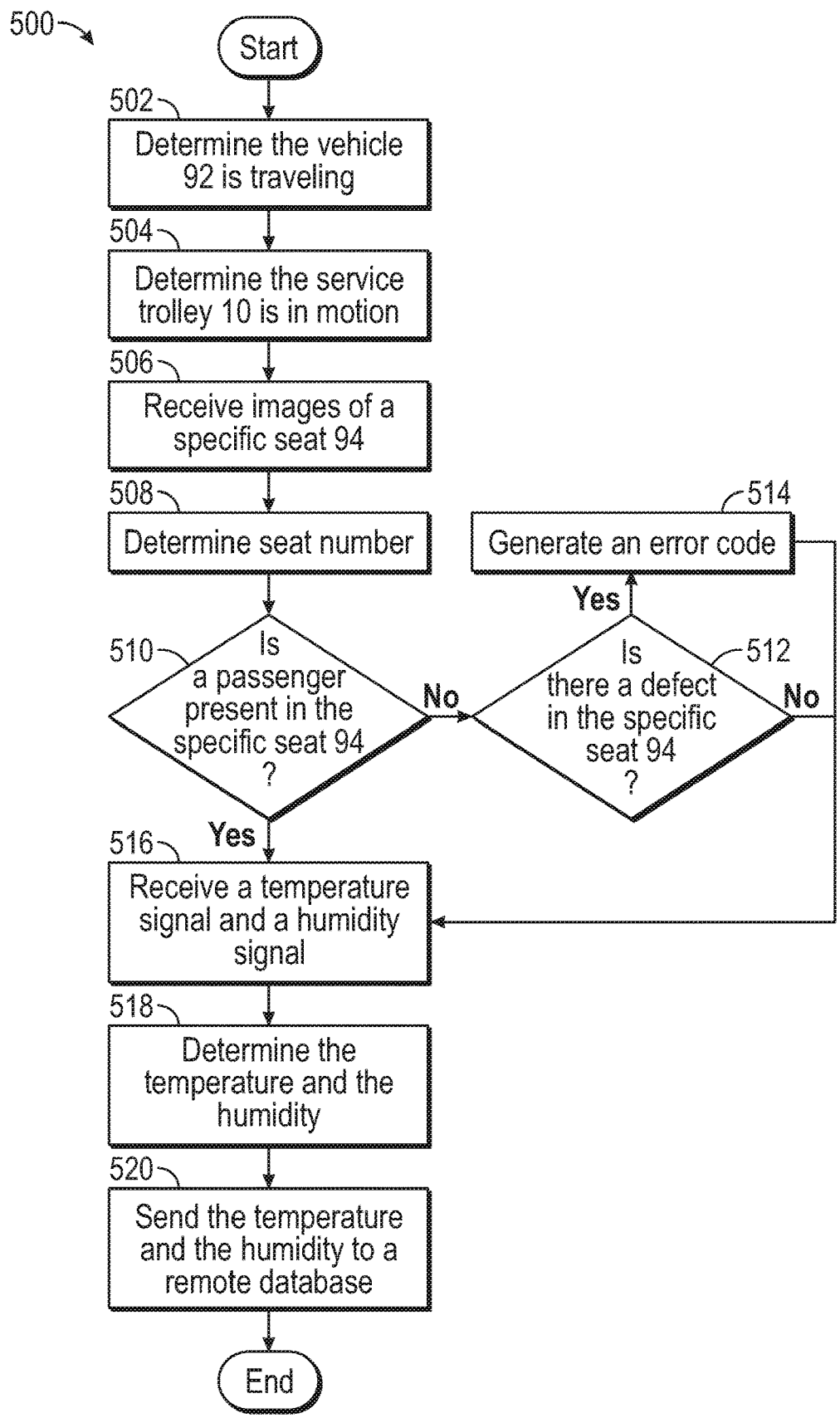
FIG. 5 is an exemplary process flow diagram illustrating a method for operating the service trolley when the vehicle is traveling according to an exemplary embodiment.
Figure 6:
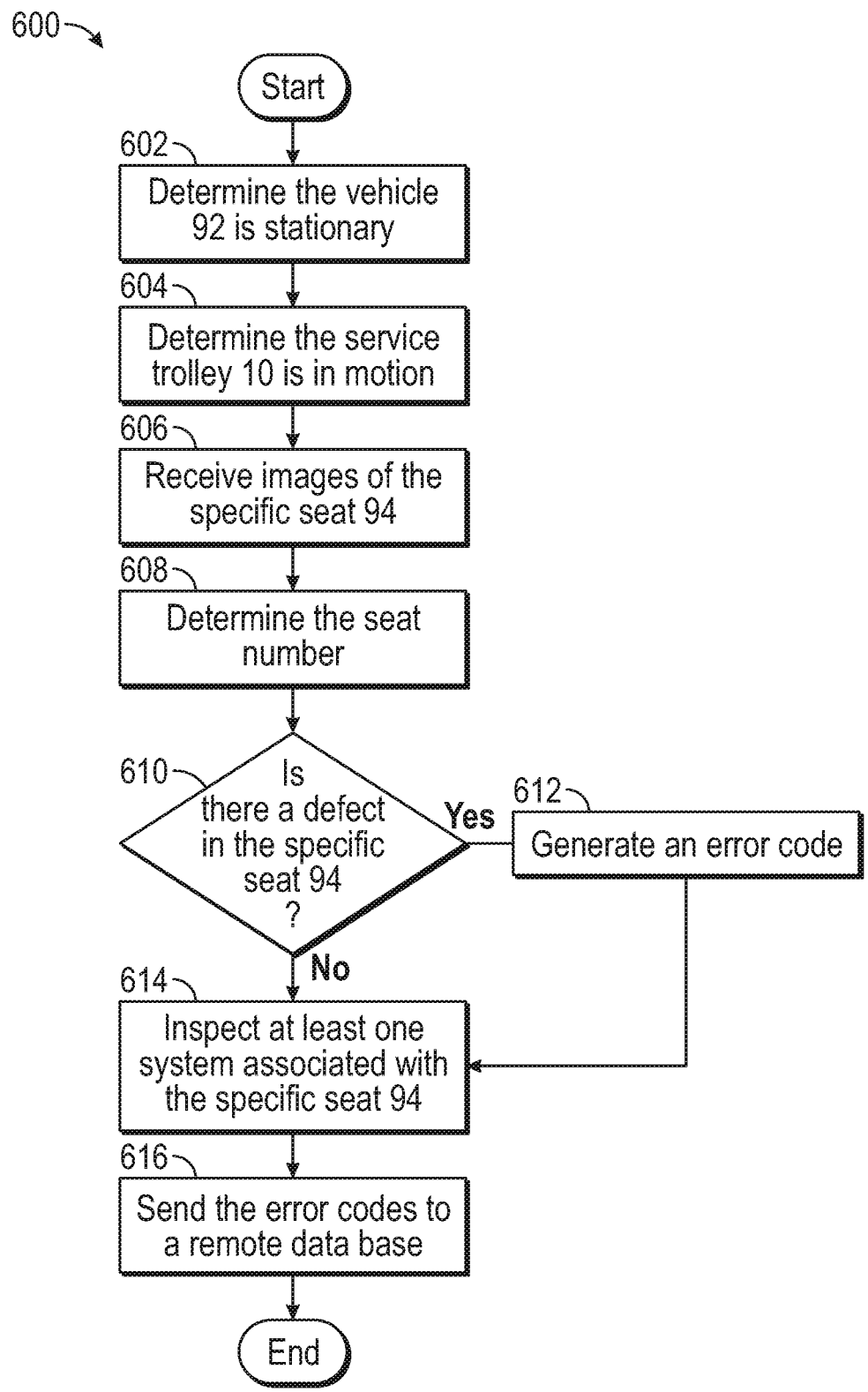
FIG. 6 is an exemplary process flow diagram illustrating a method for operating the service trolley when the vehicle is stationary according to an exemplary embodiment.

The inspection process followed when the vehicle 92 is traveling is illustrated in FIG. 5, and the inspection process followed when the vehicle 92 is stationary (e.g., grounded) is illustrated in FIG. 6. The processes for inspecting the vehicle 92 is explained in greater detail below. Referring now to FIGS. 1 and 3, when the vehicle 92 is traveling the control module 40 of the service trolley 10 determines a temperature and an ambient humidity of a specific location in the interior cabin 90 of the vehicle 92 that is proximate to the specific seat 94 being inspected for defects. The temperature is determined based on a temperature signal received from the temperature sensor 60 and the humidity signal is based on a humidity signal received from the humidity sensor 62. The temperature signal and the humidity signal are sent to the control module 40, and the control module 40 determines the temperature and the ambient humidity of the specific location of the interior cabin 90 proximate to the specific seat 94 based on the temperature signal and the humidity signal. As explained in greater detail below, the control module 40 then determines functionality of an environmental control system 120 (FIG. 4) based on the temperature and humidity. When the vehicle 92 is stationary, the control module 40 of the service trolley 10 inspects a plurality of sub-systems associated with the specific seat 94 being inspected for defects, which is also explained below.

FIG. 4 is a schematic diagram of the control module 40 in wireless communication with a plurality of control modules 140, 142, 144, 146, 148 of the specific seat 94 located within the interior cabin 90 of the vehicle 92 via the wireless network. In the embodiment as illustrated, the specific seat 94 includes a seat control module 140, a lighting control module 142, an entertainment control module 144, an environmental control system (ECS) control module 146, and a dimmable window control module 148. However, it is to be appreciated that the control modules 140, 142, 144, 146, 148 are exemplary in nature. Instead, in another embodiment a seat includes other additional control modules or fewer control modules.

The control module 40 is also in wireless communication with database 84 and cloud storage 180 via the wireless network 74. In an embodiment, the cloud storage 180 is located off-site and is not on the vehicle 92. However, in an alternative embodiment the cloud storage 180 is located on the vehicle 92.

The seat control module 140 is in electronic communication with a seat actuator 160. When the vehicle 92 is traveling, a passenger may select a button 162 or other indicator on his or her seat 94 to either recline or return to a seat back 164 to an upright position. The seat control module 140 is in electronic communication with the button 162. Thus, in response to a passenger selecting the button 162 the seat control module 140 instructs the seat actuator 160 to generate the motion required to actuate a seat back 162 of the specific seat 94 into either a reclined or an upright position.

The control module 40 of the service trolley 10 generates a seat actuation signal configured to instruct the seat control module 140 of the specific seat 94 to actuate the seat actuator 160 to the reclined and upright positions. In other words, the seat actuation signal instructions the seat actuator 160 to move the seat back 164 from the upright position into the reclined position and then back into the upright position. The seat actuation signal is sent over the wireless network 74 to the seat control module 140. In response to receiving the seat actuation signal, the seat control module 140 instructs the seat actuator 160 to move the seat back 164 into the reclined and upright position.

The control module 40 then receives a return signal over the wireless network 74. The return signal is generated by the seat control module 140 and indicates the seat actuator 160 is either operational or non-operational. Specifically, if the seat actuator 160 is unable to move the seat back 164 into the reclined and upright position, then the seat actuator 160 is non-operational. In response to determining the seat actuator 160 is non-operational, the control module 40 generates an error code indicating the seat actuator 160 is non-operational. The control module 40 transmits the error code over the wireless network 74 to the database 84 and cloud storage 180.

The lighting control module 142 is in electronic communication with at least one lighting element 166 associated with the specific seat 94. For example, in one embodiment the lighting element 166 is an overhead reading light having a switch 168. The switch 168 is in communication with the lighting control module 142. Thus, when a passenger selects the switch 168 the lighting control module 142 instructs the lighting element 166 to either illuminate (i.e., turn on) or turn off. In one embodiment, the lighting control module 142 also instructs the lighting element 166 to either increase or decrease intensity (i.e., dimming). In some embodiments the lighting element 166 is a light emitting diode. Therefore, in at least one embodiment the lighting control module 142 instructs the lighting element 166 to change frequency, which in turn changes the color of the light emitted.

The control module 40 of the service trolley 10 generates a lighting signal configured to instruct the lighting control module 142, which is associated with the specific seat 94, to illuminate the lighting element 166. The lighting signal then instructs the lighting element 166 to turn off. Alternatively, in another embodiment the lighting signal instructs the lighting element 166 to dim or change frequency. The lighting signal is sent over the wireless network to the lighting control module 142. In response to receiving the lighting signal, the lighting control module 142 instructs the lighting element 166 to illuminate and then turn off. In some embodiments, the lighting control module 142 also instructs the lighting element 166 to dim or change frequency as well.

The control module 40 then receives a return signal from the lighting control module 142. The return signal indicates the lighting element 166 is either operational or non-operational. Specifically, in one embodiment the return signal indicates that the lighting element 166 is non-operational because the lighting element 166 is unable to illuminate and then turn off The return signal also indicates if the lighting element 166 is non-operational when the lighting element 166 is unable to dim or change frequency. In response to determining that the lighting element 166 is non-operational, the control module 40 generates an error code. The error code indicates specific details such as, for example, if the lighting element 166 is unable to illuminate, dim, or change frequency. As mentioned above, control module 40 transmits the error code over the wireless network 74 to the database 84 and cloud storage 180.

The entertainment control module 144 is in electronic communication with at least one personal media device 170. Some examples of media devices 170 include, but are not limited to, a video system and an audio system. For example, the personal media device 170 includes a video screen 172 for viewing movies or the moving map of the flight. In an embodiment, the video screen is a touchscreen that displays video games. In some embodiments, the audio system includes a headphone input 174. The personal media device 170 includes a power button 176 in electronic communication with the entertainment control module 144. Thus, when a passenger in the specific seat 94 selects the power button 176, the entertainment control module 144 provides power to turn the personal media device 170 on. The entertainment control module 144 also control operation of the personal media device 170 as well. For example, the entertainment control module 144 controls the volume of the audio system and the visual images displayed upon the video screen 172.

The control module 40 of the service trolley 10 generates a power signal configured to instruct the entertainment control module 144 to commence operation of the personal media device 170. In one embodiment, the power signal instructs the personal media device 170 to change the volume and to select a specific program that is displayed upon the video screen. The power signal is sent over the wireless network to the entertainment control module 144. In response to receiving power signal, the entertainment control module 144 instructs the personal media device 170 to power on and off. In some embodiments, the entertainment control module 144 also instructs the personal media device 170 to adjust the volume and select a specific program or image to be displayed upon the video screen 172.

The control module 40 then receives the return signal from the entertainment control module 144. The return signal indicates the personal media device 170 is either operational or non-operational. Specifically, in one embodiment the return signal indicates the personal media device 170 is non-operational when the personal media device 170 is unable to power on and off. In another example, the personal media device 170 is non-operational when the volume is unable to be adjusted, or when the video screen 172 is unable to display images. In response to determining that the personal media device 170 is non-operational, the control module 40 generates an error code. The error code indicates the specific issue with the personal media device 170 such as power, audio function, or video function. As mentioned above, control module 40 transmits the error code over the wireless network 74 to the database 84 and cloud storage 180.

The ECS control module 146 is in electronic communication with a plurality of valves 178 located within ductwork 185 of the vehicle 92. The ductwork 185 provides a majority of the conditioned air that is supplied to the interior cabin 90. The ECS control module 146 regulates the amount of air exiting one or more vents 182 and into the interior cabin 90 by actuating the valves 178. The ECS control module 146 is not associated with a specific seat 94 within the vehicle 92. Instead, the control module 40 evaluates the temperature and humidity within the immediate vicinity of a specific one of the seats 94 within the vehicle 92 based on the temperature signal from the temperature sensor 60 and the humidity signal from the humidity sensor 62.

During evaluation of the interior cabin 90, the control module 40 of the service trolley 10 generates an environmental signal configured to instruct the ECS control module 146 to raise or lower the temperature of the interior cabin 90 by a predetermined amount (e.g., raise the temperature by 5° C.) by actuating the plurality of valves 178. The temperature that the interior cabin 90 is instructed to change to is referred to as a set point temperature. The environmental signal is sent over the wireless network 74 to the ECS control module 146. In response to receiving environmental signal, the ECS control module 146 actuates the valves 178 to adjust the temperature and humidity within the interior cabin 90 to the set point temperature. Although the temperature is described, a similar procedure is followed to adjust the humidity as well.

The control module 40 determines the temperature of the interior cabin 90 within immediate vicinity of the specific seat 94 based on readings from the temperature sensor 60 and the humidity sensor 62. The control module 40 then compares the temperature of the interior cabin 90 within immediate vicinity of the specific seat 94 with the set point temperature. In response to determining a difference between the set point temperature and the temperature of the interior cabin 90 within immediate vicinity of the specific seat 94 exceeds a threshold, the control module 40 generates an error code. The error code indicates the ECS of the vehicle 92 is not regulating the environment in immediate vicinity of the specific seat 94 in conformity with the entire interior cabin 90 of the vehicle 92. For example, the error code may indicate a hot spot or area within an aircraft that is unable to heat or cool properly due to an issue such as, for example, a blocked vent. As mentioned above, control module 40 transmits the error code over the wireless network 74 to the database 84 and cloud storage 180.

The dimmable window control module 148 is in electronic communication with an electrochromic glass assembly 190 that is part of a passenger window 192. A shade button 194 is in electronic communication with the glass assembly 190. The passenger window 192 darkens when more current is supplied to the glass assembly 190 and lightens when current is removed from the glass assembly 190. Thus, when a passenger in the specific seat 94 selects the shade button 194, a current signal is sent to the glass assembly 190 that either increases the current to darken the passenger window 192 or decreases current to lighten the passenger window 192, which in turn causes the passenger window 192 to darken.

The control module 40 of the service trolley 10 generates a dimming signal configured to instruct the dimmable window control module 148, which is associated with the specific seat 94, to lighten or darken the glass assembly 190 of the passenger window 192 associated with the specific seat 94. The dimming signal is sent over the wireless network to the dimmable window control module 148. In response to receiving the lighting signal, the dimmable window control module 148 instructs the glass assembly 190 to either lighten or darken by adjusting the current.

The control module 40 then receives the return signal from the dimmable window control module 148. The return signal indicates the glass assembly 190 of the passenger window 192 associated with the specific seat 94 is either operational or non-operational. Specifically, if the glass assembly 190 is unable to lighten or darken in response to changing current, then the glass assembly 190 is non-operational. In response to determining that the glass assembly 190 is non-operational, the control module 40 generates an error code. As mentioned above, control module 40 transmits the error code over the wireless network 74 to the database 84 and cloud storage 180.

In some instances, the control module 40 does not receive the return signal over the wireless network 74 by one of the control modules. In other words, the seat control module 140, the lighting control module 142, the entertainment control module 144, or the dimmable window control module 148 do not generate a return signal indicating that the corresponding system is operational or non-operational. Instead, the control module 40 of the service trolley 10 is responsible for determining if a corresponding system is operational or non-operational. Specifically, the control module 40 determines the corresponding system is operational or non-operational by analyzing a plurality of images of the specific system under test. When a system is under test, one or more components of the system operates based on the signal sent from the control module 40. For example, when the passenger window 192 is under test, the glass assembly 190 operates based on the dimming signal generated by the control module 40 (i.e., the glass assembly 190 either lightens or darkens).

Operation of the control module 40 to determine if a system is operational or non-operational is now explained. First, the control module 40 generates a testing signal configured to instruct at least one component associated with the specific seat 94 to operate under a testing sequence. For example, if the testing signal is the seat actuation signal, then the components include the seat actuator 160 and the seat back 164 of the specific seat 94. In response to receiving the testing signal, the component operates under the testing sequence. In the present example, the component is the seat actuator 160 and the seat back 164, and the testing sequence includes having the seat actuator 160 move the seat back 164 back and forth between the reclined and upright positions.

As the component of the specific seat 94 operates under the testing sequence, the control module 40 receives a plurality of images of the components operating from the image capture devices 32. In the present example, the control module 40 receives a plurality of images of the seat back 164 moving back and forth between the reclined and upright position.

The control module 40 executes image processing logic for analyzing the plurality of images of the component operating under the testing sequence and determines completion of the testing sequence based on the analysis. In the present example, the control module 40 executes image processing logic to analyze the images of the seat back 164. The testing sequence includes actuating the seat back 164 between the reclined and the upright position. If the seat actuator 160 is broken or otherwise non-operational, then the seat back 164 may not move back and forth at all or, alternatively, the seat back 164 may only complete partial movement (e.g., the seat back 164 may recline but is unable to return to the upright position). Accordingly, the control module 40 determine the testing sequence was not completed successfully.

The control module 40 determines the component operating under the testing sequence is operational or non-operational based on the completion of the testing sequence. In response to determining the component is non-operational, the control module 40 generates an error code. For example, if the control module 40 determines the seat actuator 160 is non-operational, then the control module 40 generates a specific error code indicating a non-function seat actuator for the specific seat 94. Referring to both FIGS. 3 and 4, in one example the control module 40 of the service trolley 10 would generate an error code indicating that the seat actuator associated with seat 4C is non-operational.

Although the seat actuator 160 is described in the present example, the control module 40 also evaluates other components based on image processing logic as well. For example, the in one embodiment control module 40 executes image processing logic to confirm the lighting element 166 illuminates, dims, and/or changes frequency. In another example, the control module 40 monitors the video screen 172 of the personal media device 170 and confirms the personal media device 170 powers on and off. In one embodiment, the control module 40 confirms a specific program or image is displayed upon the video screen 172. In yet another example, the control module 40 monitors the passenger window 192 to confirm operation of the electrochromic glass assembly 190.

FIG. 5 is an exemplary process flow diagram illustrating a method 500 for operating the service trolley 10 when the vehicle 92 is traveling. In the event the vehicle 92 is an aircraft, then the aircraft is in cruise. Referring generally to FIGS. 1 and 3-5, the method 500 begins at block 502. In block 502, the control module 40 of the service trolley 10 determines that the vehicle 92 is traveling based on an operational signal. Specifically, the antenna 36 is connected to the wireless network 74 to receive the operational signal. The operational signal is generated by one of the control modules 76 of the vehicle 92 and indicates the vehicle 92 is traveling. The operational signal is sent over the wireless network 74 and is received by the antenna 36. In one embodiment, the vehicle 92 is an aircraft and the operational signal indicates the aircraft is in cruise. The method 500 may then proceed to block 504.

In block 504, the control module 40 receives the motion signal from the accelerometer 88. The control module 40 determines the service trolley 10 is in motion in response to receiving the motion signal. In other words, the service trolley 10 is removed from a storage compartment (e.g., the galley 102 in FIG. 1) and is now positioned within the aisleway 100. The method 500 may then proceed to block 506.

In block 506, the control module 40 receives an image of the specific seat 94 from the image capture devices 32. The method 500 may then proceed to block 508.

In block 508, the control module 40 determines the seat number of the specific seat 94 that is about to be inspected. In one embodiment, the image of the specific seat includes a corresponding seat number and the control module 40 executes image processing logic to determine the corresponding seat number of the specific seat 94. This is because the seat number is sometimes visible along a side of a seat.

In another approach when the seat number is obstructed from view or is not present, the control module 40 receives a signal over the wireless network 74 from the vehicle control module 76. The signal includes a map or diagram of the interior cabin 90 of the vehicle 92. The control module 40 receives the positional signal from the position sensor 86, which indicates the relative position of the service trolley 10 within the interior cabin 90 of the vehicle 92. The control module 40 then determines the position of the service trolley 10 based on the signal received over the wireless network 74 and the positional signal. The method 500 may then proceed to block 510.

In block 510, the control module 40 compares the image data stored in the database 80 with the image of the specific seat 94 from the image capture devices 32 of the specific seat 94 and determines the presence of a passenger seated within the seat 94 based on the comparison. Specifically, if a passenger is present in the specific seat 94, the image data representative of the specific seat 94 stored in the database 80 will not substantially correspond with the image of the specific seat 94 that is taken by the image capture devices 32.

In response to determining the absence of a passenger in the specific seat 94, the method 500 proceeds to block 512. In block 512, the control module 40 determines a presence of at least one defect on an exterior of the specific seat 94. If no defect is found, then the method 500 proceeds to block 516. However, in response to determining the presence of at least one defect along the exterior of the specific seat 94, the method 500 proceeds to block 514.

In block 514, the control module 40 generates an error code indicating the presence of the defect on the exterior of the specific seat 94. In an embodiment, unique error codes are assigned to each type of defect. For example, a tear in the seat may be assigned one error code and a missing seat cushion is assigned another error code. The control module 40 transmits the error code over the wireless network 74 to the database 84 and cloud storage 180. The method 500 may then proceed to block 516.

In block 516, the control module 40 receives the temperature signal from the temperature sensor 60 and the humidity signal from the humidity sensor 62. The control module 40 then determines the temperature and the ambient humidity of a specific location within the interior cabin 90 based on the temperature signal and the humidity signal, where the specific location is proximate to the specific seat 94. The method 500 may then proceed to block 518.

In block 518, the control module 40 transmits the temperature, the humidity, and the seat number associated with the specific seat 94 over the wireless network 74 to a remote database, such as the database 84 and cloud storage 180. The temperature and humidity readings are used to determine an overall temperature and humidity pattern of various locations within the interior cabin 90 of the vehicle 92. In one example, if the vehicle 92 is an aircraft, the temperature and humidity patterns are used to regulate the ECS of the aircraft. The method 500 may then terminate.

FIG. 6 is an exemplary process flow diagram illustrating a method 600 of inspecting the interior cabin 90 of the vehicle 92 by the service trolley 10 when the vehicle 92 is stationary. For example, if the vehicle 92 is an aircraft, then the aircraft is grounded. Referring generally to FIGS. 1, 3-4, and 6, the method 600 may begin at block 602. In block 602, the control module 40 of the service trolley 10 determines that the vehicle 92 is stationary based on the operational signal. The method 600 may then proceed to block 604.

In block 604, the control module 40 receives the motion signal from the accelerometer 88. The control module 40 determines the service trolley 10 is in motion in response to receiving the motion signal. The method 600 may then proceed to block 606.

In block 606, the control module 40 receives an image of the specific seat 94 from the image capture devices 32. The method 600 may then proceed to block 608.

In block 608, the control module 40 determines the seat number of the specific seat 94 that is about to be inspected, which is described in greater detail above with respect to the method 500 shown in FIG. 5. The method 600 may then proceed to block 610.

In block 610, the control module 40 compares the image data stored in the database 80 with the image of the specific seat 94 from the image capture devices 32 and determines a presence of at least one defect on an exterior of the specific seat 94. If no defect is found, then the method 600 proceeds to block 614. However, in response to determining the presence of at least one defect along the exterior of the specific seat 94, the method 600 proceeds to block 612.

In block 612, the control module 40 generates an error code indicating the presence of the defect on the exterior of the specific seat 94. As explained above, unique error codes are assigned to each type of defect. The method 600 may then proceed to block 614.

In block 614, the control module 40 inspects one or more systems associated with the specific seat 94. Referring now to FIG. 4, in one embodiment the control module 40 inspects at least one of the following, the seat control module 140, the lighting control module 142, the entertainment control module 144, the ECS control module 146, and the dimmable window control module 148. The method 600 may then proceed to block 616.

In block 616, if the control module 40 receives one or more return signals indicating a system is non-operational, the control module generates an error code. The control module 40 transmits the error code over the wireless network 74 to a remote database, such as the database 84 and cloud storage 180. The method 600 may then terminate.

Referring generally to the figures, technical effects and benefits of the disclosed trolley cart include reduced costs and increased productivity. Conventional approaches for inspecting the interior cabin of an aircraft require several personnel who have received specialized training. The personnel test the seats and their related accessories in an aircraft manually. This approach is time consuming and expensive because of the labor costs associated with inspecting the seats manually. In contrast, the disclosed trolley cart requires less effort and time to operate by personnel. In fact, if the service trolley is autonomous then the service trolley may not require human input to operate.

The description of the present disclosure is merely exemplary in nature and variations that do not depart from the gist of the present disclosure are intended to be within the scope of the present disclosure. Such variations are not to be regarded as a departure from the spirit and scope of the present disclosure.

What is claimed is:

1. A service trolley for inspecting an interior cabin of a vehicle including a plurality of seats, the service trolley comprising:
   a container body supported by a plurality of wheels, wherein the service trolley defines an outer surface;
   at least one image capture device mounted to the container body and positioned along the outer surface of the container body in a location relative to the interior cabin of the vehicle to view the plurality of seats; and
   a control module in electronic communication with the at least one image capture device and a database storing image data representative of the plurality of seats of the vehicle, the control module executing instructions to:
   receive an image of a specific seat from the at least one image capture device;
   compare the image data stored in the database with the image of the specific seat to determine a presence of at least one defect on an exterior of the specific seat in the interior cabin of the vehicle; and
   in response to determining the presence of at least one defect along an exterior of one of the plurality of seats, generate an error code indicating the presence of the at least one defect on the exterior of the specific seat.

2. The service trolley of claim 1, further comprising an antenna in electronic communication with the control module, wherein the antenna is connected to a wireless network to receive an operational signal indicating the vehicle is either traveling or is stationary.

3. The service trolley of claim 2, further comprising a temperature sensor and a humidity sensor in electronic communication with the control module, wherein the control module executes instructions to:
   determine the vehicle is traveling based on the operational signal;
   in response to determining the vehicle is traveling, receive a temperature signal from the temperature sensor and a humidity signal from the humidity sensor;
   determine a temperature and a humidity of a specific location within the interior cabin based on the temperature signal and the humidity signal, wherein the specific location within the interior cabin is proximate to the specific seat; and
   transmit the temperature and the humidity over the wireless network to a remote database.

4. The service trolley of claim 2, wherein the control module executes instructions to:
   determine the vehicle is stationary based on the operational signal;
   in response to determining the vehicle is stationary, generate a seat actuation signal that is configured to instruct a seat control module of the specific seat to actuate a seat actuator;
   send the seat actuation signal over the wireless network to the seat control module;
   receive a return signal from the seat control module of the specific seat, wherein the return signal indicates the seat actuator is either operational or non-operational; and
   in response to determining the seat actuator is non-operational, generate an error code.

5. The service trolley of claim 2, wherein the control module executes instructions to:

determine the vehicle is stationary based on the operational signal;
in response to determining the vehicle is stationary, generate a lighting signal configured to instruct a lighting control module associated with the specific seat to illuminate a lighting element;
send the lighting signal over the wireless network to the lighting control module;
receive a return signal from the lighting control module, wherein the return signal indicates the lighting element is either operational or non-operational; and
generate an error code in response to determining the lighting element is non-operational.

6. The service trolley of claim 5, wherein the error code indicates at least one of:
the lighting element is unable to illuminate and then turn off;
the lighting element is unable to dim; and
the lighting element is unable to change frequency.

7. The service trolley of claim 2, wherein the control module executes instructions to:
determine the vehicle is stationary based on the operational signal;
in response to determining the vehicle is stationary, generate a power signal configured to instruct an entertainment control module to commence operation of a personal media device associated with the specific seat;
send the power signal over the wireless network to the entertainment control module;
receive a return signal from the entertainment control module of the specific seat, wherein the return signal indicates the personal media device is either operational or non-operational; and
in response to determining the personal media device is non-operational, generate an error code.

8. The service trolley of claim 2, wherein the control module executes instructions to:
determine the vehicle is stationary based on the operational signal;
in response to determining the vehicle is stationary, generate a testing signal configured to instruct at least one component associated with the specific seat to operate under a testing sequence;
receive a plurality of images of the at least one component operating from the at least one image capture device;
analyze the plurality of images of the at least one component operating under the testing sequence;
determine the at least one component operating under the testing sequence is operational or non-operational based on completion of the testing sequence; and
in response to determining the at least one component is non-operational, generate an error code.

9. The service trolley of claim 2, further comprising a temperature sensor in electronic communication with the control module, wherein the control module executes instructions to:
determine the vehicle is stationary based on the operational signal;
in response to determining the vehicle is stationary, generate an environmental signal configured to instruct an environmental control system (ECS) control module to raise or lower a temperature of the interior cabin by a predetermined amount;
determine a temperature of the interior cabin within immediate vicinity of the specific seat based on readings from the temperature sensor;
compare the temperature of the interior cabin within immediate vicinity of the specific seat with a set point temperature;
determine a difference between the set point temperature and the temperature of the interior cabin within immediate vicinity of the specific seat exceeds a threshold; and
in response to determining the difference exceeds the threshold, generate an error code.

10. The service trolley of claim 2, wherein the control module executes instructions to:
determine the vehicle is stationary based on the operational signal;
in response to determining the vehicle is stationary, generate a dimming signal configured to instruct a dimmable window control module to lighten or darken an electrochromic glass assembly of a passenger window associated with the specific seat;
send the dimming signal over the wireless network to the dimmable window control module;
receive a return signal from the dimmable window control module of the specific seat, wherein the return signal indicates the electrochromic glass assembly is either operational or non-operational; and
in response to determining the electrochromic glass assembly is non-operational, generate an error code.

11. The service trolley of claim 1, further comprising:
a plurality of wheels supporting the container body; and
a wheel assist device in communication with the control module, wherein the wheel assist device is configured to control rotation of the plurality of wheels.

12. The service trolley of claim 11, wherein the wheel assist device is configured to autonomously control the service trolley by manipulating the plurality of wheels.

13. A method of inspecting an interior cabin of a vehicle including a plurality of seats by a service trolley, the method comprising:
receiving, by a control module of the service trolley, an image of a specific seat from at least one image capture device, wherein the at least one image capture device is mounted to a container body of the service trolley is and positioned along an outer surface of the container body in a location relative to the interior cabin of the vehicle to view the plurality of seats;
comparing, by the control module of the service trolley, image data stored in a database with the image of the specific seat;
determining a presence of at least one defect on an exterior of the specific seat in the interior cabin of the vehicle based on comparing the image data stored in the database with the image of the specific seat; and
in response to determining the presence of at least one defect along an exterior of one of the plurality of seats, generating an error code indicating the presence of the at least one defect on the exterior of the specific seat.

14. The method of claim 13, further comprising:
receiving, by an antenna in electronic communication with the control module, an operational signal indicating the vehicle is either traveling or is stationary.

15. The method of claim 14, further comprising:
determining, by the control module of the service trolley, the vehicle is traveling based on the operational signal;
in response to determining the vehicle is traveling, receiving a temperature signal from a temperature sensor and a humidity signal from a humidity sensor by the control module of the service trolley;

determining a temperature and a humidity of a specific location within the interior cabin based on the temperature signal and the humidity signal, wherein the specific location within the interior cabin is proximate to the specific seat; and transmitting, by the control module of the service trolley, the temperature and the humidity over a wireless network to a remote database.

16. The method of claim 14, further comprising:

determining, by the control module of the service trolley, the vehicle is stationary based on the operational signal;

in response to determining the vehicle is stationary, generating a seat actuation signal configured to instruct a seat control module of the specific seat to actuate a seat actuator;

sending the seat actuation signal over a wireless network to the seat control module;

receiving, by the control module of the service trolley, a return signal from the seat control module of the specific seat, wherein the return signal indicates the seat actuator is either operational or non-operational; and in response to determining the seat actuator is non-operational, generating an error code by the control module of the service trolley.

17. The method of claim 14, further comprising:

determining, by the control module of the service trolley, the vehicle is stationary based on the operational signal;

in response to determining the vehicle is stationary, generating a lighting signal configured to instruct a lighting control module associated with the specific seat to illuminate a lighting element;

sending the lighting signal over a wireless network to the lighting control module;

receiving, by the control module of the service trolley, a return signal from the lighting control module, wherein the return signal indicates the lighting element is either operational or non-operational; and in response to determining the lighting element is non-operational, generating an error code by the control module of the service trolley.

18. The method of claim 14, further comprising:

determining, by the control module of the service trolley, the vehicle is stationary based on the operational signal;

in response to determining the vehicle is stationary, generating a power signal configured to instruct an entertainment control module to commence operation of a personal media device associated with the specific seat;

sending the power signal over a wireless network to the entertainment control module;

receiving, by the control module of the service trolley, a return signal from the entertainment control module of the specific seat, wherein the return signal indicates the personal media device is either operational or non-operational; and in response to determining the personal media device is non-operational, generating an error code by the control module of the service trolley.

19. The method of claim 14, further comprising:

determining, by the control module of the service trolley, the vehicle is stationary based on the operational signal;

in response to determining the vehicle is stationary, generating a testing signal configured to instruct at least one component associated with the specific seat to operate under a testing sequence;

receiving a plurality of images of the at least one component operating from the at least one image capture device;

analyzing, by the control module of the service trolley, the plurality of images of the at least one component operating under the testing sequence;

determining the at least one component operating under the testing sequence is operational or non-operational based on completion of the testing sequence; and in response to determining the at least one component is non-operational, generating an error code by the control module of the service trolley.

20. The method of claim 14, further comprising:

determining, by the control module of the service trolley, the vehicle is stationary based on the operational signal;

in response to determining the vehicle is stationary, generating an environmental signal configured to instruct an ECS control module to raise or lower a temperature of the interior cabin by a predetermined amount;

determining the temperature of the interior cabin within immediate vicinity of the specific seat based on readings from a temperature sensor;

comparing the temperature of the interior cabin within immediate vicinity of the specific seat with a set point temperature;

determining, by the control module of the service trolley, a difference between the set point temperature and the temperature of the interior cabin within immediate vicinity of the specific seat exceeds a threshold; and in response to determining the difference exceeds the threshold, generating an error code by the control module of the service trolley.

* * * * *